United States Patent

Kida et al.

[11] Patent Number: 5,828,500
[45] Date of Patent: Oct. 27, 1998

[54] OPTICAL ELEMENT INSPECTING APPARATUS

[75] Inventors: Atsushi Kida; Masato Hara; Masayuki Sugiura; Toshihiro Nakayama, all of Tokyo, Japan

[73] Assignee: Asahi Kogaku Kogyo Kabushiki Kaisha, Tokyo, Japan

[21] Appl. No.: 728,182

[22] Filed: Oct. 9, 1996

[30] Foreign Application Priority Data

| Oct. 11, 1995 | [JP] | Japan | 7-263327 |
| Dec. 14, 1995 | [JP] | Japan | 7-326121 |
| Jul. 11, 1996 | [JP] | Japan | 8-182557 |
| Jul. 11, 1996 | [JP] | Japan | 8-182558 |

[51] Int. Cl.$^6$ .............................. G02B 7/02; G01J 21/00
[52] U.S. Cl. .......................... 359/798; 359/799; 359/800; 356/237
[58] Field of Search ................................ 359/798, 799, 359/800, 821, 822; 356/351, 364, 365, 127, 237, 239

[56] References Cited

U.S. PATENT DOCUMENTS

| 5,216,481 | 6/1993 | Minato | 356/240 |
| 5,333,052 | 7/1994 | Finarov | 356/369 |
| 5,504,581 | 4/1996 | Natata et al. | 356/364 |
| 5,532,823 | 7/1996 | Fukui et al. | 356/364 |
| 5,604,591 | 2/1997 | Kitagawa | 356/351 |

*Primary Examiner*—George Y. Epps
*Assistant Examiner*—Ricky Mack
*Attorney, Agent, or Firm*—Greenblum & Bernstein P.L.C.

[57] ABSTRACT

An optical element inspecting apparatus for inspecting optical elements for defects. The optical element inspecting apparatus includes an illuminating unit, an image capturing unit, two polarizers, a rotation device, a controller, and a means for composing a plurality of image data captured by the image capturing unit.

The optical element to be inspected is placed between the polarizers and is illuminated by the illuminating unit. The light that passes through the polarizers and the optical element is captured by the image capturing unit and stored in memory. The controller controls the rotation device such that the polarizers are rotated by a predetermined amount and a subsequent image data is captured. In this way, a number of image data are captured and all image data are composed to make a composite image data. The optical element is examined to detect flaws therein by using the composite image data.

23 Claims, 17 Drawing Sheets

OPTICAL ELEMENT INSPECTING APPARATUS

BACKGROUND OF THE INVENTION

The present invention relates to an optical element inspecting apparatus for detecting optical defects in optical elements, such as lenses, and particularly concerns an apparatus for inspecting for the existence of birefringence due to strain.

Optical elements such as lenses, optical parallel plates or prisms made from glass or plastic may be subject to various types of strain caused by factors, such as mechanical tension, compression or shear due to internal stress, and/or improper cooling or improper annealing during manufacture of the optical element.

In particular, an optical element made of a resin material using a molding die tends to have birefringence due to strain of orientation of high polymer (e.g., a high molecular weight polymer) adjacent to a gate.

Strain causes birefringence. If, for example, a lens in an imaging optical system has birefringence, a sharp image cannot be formed. Further, strain may cause the lens itself to break. Thus, it is necessary to inspect for strain in optical elements and to reject any optical elements that are subject to an unacceptable amount of strain.

Conventionally, a device known as a polariscope is used to detect strain in an optical element. The conventional polariscope comprises a pair of polarizers having perpendicular transmission axes. A lens to be tested (test lens) is arranged between the polarizers and is illuminated by a light source located opposite the eye of an inspector. The inspector then examines the lens by observing the light passed through the polarizers.

If the lens has birefringence, the brightness distribution in the lens area examined by the inspector is not uniform, and the degree of the non-uniformity varies in accordance with the degree of birefringence. As such, the inspector can determine whether the test lens is acceptable or not based on the degree of the non-uniformity of the brightness distribution.

However, inspection using the conventional polariscope is a subjective test, that is, the standard for judgment varies according to the current inspector.

A further problem of the conventional polariscope is that detection of birefringence is performed for one direction only. Since the effects of birefringence produce different brightness distributions depending on the direction of incident linearly polarized light, it is difficult to determine the overall effects of birefringence in a conventional inspection.

A still further problem is that several types of flaws, including inhomogeneous refractive power distribution in the element, depressions caused by separation of the resin material from the surface of the molding die, flaw marks (in the form of ripples) caused by a contraction of the resin, or dust attached to the lens surface cannot be detected by an inspection using the conventional polariscope.

SUMMARY OF THE INVENTION

It is therefore an object of the present invention to provide an improved optical element inspecting apparatus that detects the effects of birefringence in an optical element to be inspected at any angle or direction.

Another object of the present invention is to provide an optical element inspecting apparatus which can inspect the optical element based on the objective standard of judgment.

According to one aspect of the present invention, the optical element inspecting apparatus comprises: an illuminating unit for illuminating the optical element, an image capturing unit which receives light output by the illuminating unit via the optical element, two polarizers located in an optical path between the illuminating unit and the image capturing unit positioned such that the optical element is located between the polarizers, a rotation device for rotating the polarizers so that the transmission axes of the polarizers rotate in planes which cross the optical path while keeping a constant angle between the transmission axes thereof, a controller for controlling the image capturing unit and the rotation device to capture data of images formed by the light transmitted through the polarizers and the optical element at a plurality of different rotational positions of the polarizers, wherein the controller composes the image data captured by the image capturing unit.

The optical element to be tested may be, for example, a lens, a plate or a prism made from, for example, glass or plastic.

According to another aspect of the present invention, the optical element inspecting apparatus comprises: an illuminating unit for illuminating an optical system including at least an optical element to be tested, an image capturing unit located opposite to the illuminating unit with the optical system therebetween, a light intercepting member located between the illuminating unit and the optical system to intercept a part of the light emitted from the illuminating unit, a pair of polarizers located in an optical path between the illuminating unit and the image capturing unit positioned such that that the optical system is located between the pair of polarizers, a rotation device for rotating the pair of polarizers so that the transmission axes of the pair of polarizers rotate in planes crossing the optical path while keeping a constant angle between the transmission axes thereof, and a controller for controlling the image capturing unit and the rotation device to capture data of images formed by the light transmitted through the pair of polarizers and the optical system for a plurality of different rotational positions of the pair of polarizers, wherein the controller composes the image data captured by the image capturing unit.

In particular, the optical system including the optical element to be tested must have positive power as a whole. Thus, when the optical element is a positive lens, only this lens is located between the pair of polarizers. On the other hand, if the optical element is a plate having no power or a negative lens, a positive supplementary lens is required to ensure that the total optical system has positive power.

Further, the light intercepting member must be located at or near the focal point of the optical system including the optical element to be tested.

DETAILED DESCRIPTION OF THE PREFERRED EMBODIMENTS

Figure 1:
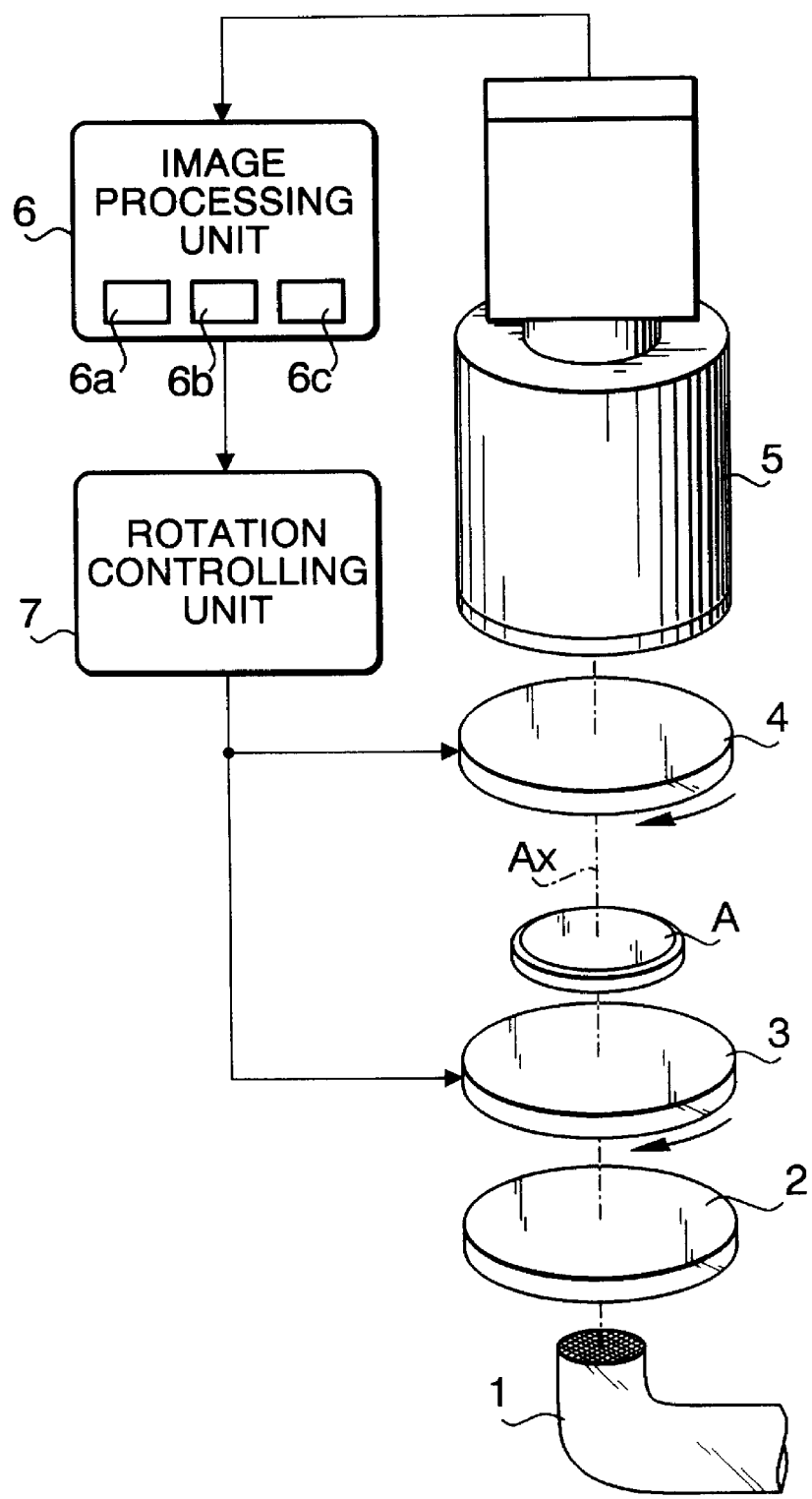
FIG. 1 shows a perspective view and block diagram of a first embodiment of the optical element inspecting apparatus.

FIG. 1 shows an optical element inspecting apparatus according to the first embodiment of the present invention.

As shown in FIG. 1, the optical element inspecting apparatus includes a light guide fiber bundle 1, a diffuser plate 2, a first polarizer 3, a second polarizer 4, a photographing unit 5, an image processing unit 6 and a rotation controlling unit 7. An optical element under inspection, for example, a test lens A, is located between the polarizers 3 and 4.

The light guide fiber bundle 1 is part of an illuminating unit. Light emitted from a light source (not shown) is guided by the light guide fiber bundle 1 and exits from the tip end of the filter bundle 1 to impinge on the diffuser plate 2.

The light emitted from the light guide fiber bundle 1 is unpolarized white light. It can be selected in accordance with the intended usage of the test lens A. For example, the light may be infrared light, ultraviolet light, or visible light having a predetermined wavelength range. However, the light should not be linearly polarized light.

The photographing unit 5 is located opposite the light guide fiber bundle 1 to receive light that has passed through the diffuser plate 2, the first polarizer 3, the test lens A and the second polarizer 4. The diffuser plate 2, the first polarizer 3, the test lens A and the second polarizer 4 are arranged on an optical path between the light guide fiber bundle 1 and the photographing unit 5.

Diffused light from the diffuser plate 2 is incident on the first polarizer 3 and is thereby transformed into linearly polarized light. The first polarizer 3 is rotatable about a rotation axis $A\chi$ so that the transmission axis of the first polarizer 3 can rotate in a plane perpendicular to the optical path. Consequently, the direction of the plane of polarization of the light exiting from the first polarizer 3 varies in accordance with the direction of the transmission axis of the first polarizer 3.

Similarly, the second polarizer 4 is rotatable about the rotation axis $A\chi$, and transmits only linearly polarized light with a plane of polarization that coincides with the transmission axis of the second polarizer 4.

The light transmitted through the second polarizer 4 impinges on the photographing unit 5.

The photographing unit 5 includes a photographing lens (not shown), which, as a whole, constitutes a positive lens system, and an image detecting element, such as a CCD area sensor (not shown). The rotation axis $A\chi$ of the polarizers is coaxial with the optical axis of the photographing lens.

The image detecting element captures data of an image formed by the photographing lens. The image detecting element and the test lens A are optically conjugate with respect to the photographing lens. That is, an image of the test lens A is formed on the image detecting element. The image detecting element is formed as, for example, a two-dimensional array of pixels (light receiving picture elements). After image data is captured, the image detecting element outputs image data as analog brightness data, i.e. gray-scale data, for each pixel.

The image data output from the image detecting element of the photographing unit 5 is sent to the image processing unit 6. The image processing unit 6 is provided with a first frame memory 6a, a second frame memory 6b, a character data memory 6c, and a temporary memory (not shown) for image processing, and is further connected to the rotation controlling unit 7.

The image processing unit 6 controls the rotation controlling unit 7 and the photographing unit 5 to capture image data at different rotational positions of the polarizers 3 and 4. In this embodiment, eight (8) frames of image data are captured for one test element at every 22.5 degrees of rotation. Namely, the polarizers 3 and 4 rotate through 180 degrees capturing eight frames of data for one test element.

Further, the image processing unit 6 emphasizes brightness differences in the image data captured by the image capturing unit 5, composes the differentiated image data, represents characteristics of patterns included in the composite image data as numerical values, and compares the numerical values with a predetermined reference values in order to judge whether the test lens A is acceptable or should be rejected.

The rotation controlling unit 7 controls motors (not shown) to rotate the first and second polarizers 3 and 4 about the rotation axis A$\chi$. The polarizers 3 and 4 rotate while keeping a constant angle between the transmission axes of the polarizers 3 and 4. In the first embodiment, the angle between the transmission axes is either 90 degrees (perpendicular condition) or 0 degrees (parallel condition). The polarizers 3 and 4 rotate to maintain a constant angle between the transmission axes during the inspection process. The polarizers 3 and 4 can also be rotated between an orientation in which the transmission axes are perpendicular to each other and an orientation in which the transmission axes are parallel during a setting.

If the angle is set to 90 degrees, i.e., when the transmission axes are perpendicular to each other, light rays passing through the test lens A without a change in the polarized state of the light rays are intercepted by the second polarizer 4, and therefore do not reach the image capturing unit 5. However, if The incident linearly polarized light changes the state of its polarization, for instance, if the incident linearly polarized light is converted to elliptically polarized light due to birefringence, or if the plane of polarization is rotated due to the optical rotation, the affected light may transmit through the second polarizer 4.

Figure 2:
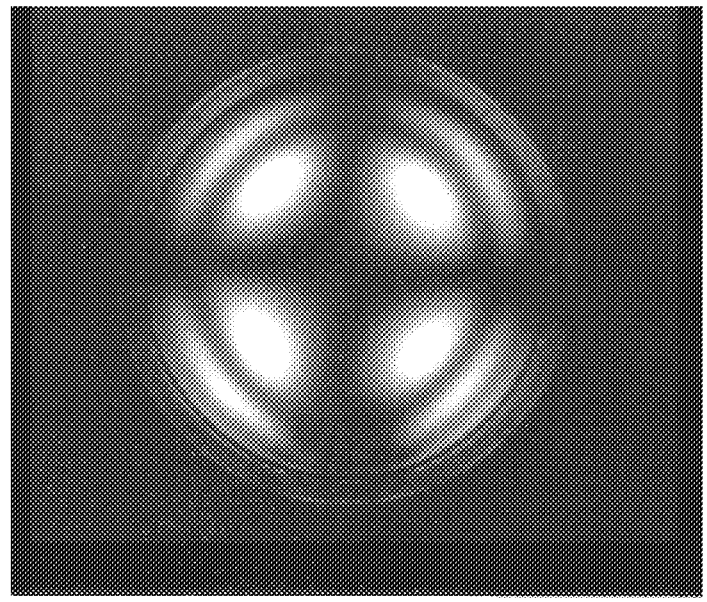
FIG. 2 is a photograph showing image data captured by the optical element inspecting apparatus before a composing process, in the case when the transmission axes of the polarizers are perpendicular.

If the test lens A has birefringence, extraordinary rays due to the birefringence may be transmitted through the second polarizer 4 and reach the image capturing unit 5, since the rays subject to birefringence have a different polarized state. Using an angle of 90 degrees (perpendicular condition), the captured image data is then displayed as shown in FIG. 2. FIG. 2 is a photograph showing the image captured data before a differentiation process and a composing process are performed, i.e., FIG. 2 shows a single photograph at one angle position of the polarizers 3 and 4. In this case, although the test lens A was known to have strain in the lower portion in the photograph, it is difficult to judge the presence of strain from FIG. 2. Most of the bright patterns (white portions) are caused by the transmission of light due to an optical rotation of the plane of polarization. The optical rotation is known as the angular displacement of the plane of polarization of light passing through an optical element.

When the optical rotation is analyzed, the incident linearly polarized light is considered as a combination of two polarizing light components. One component is a P polarized light component for which the plane of polarization is parallel to the incident plane, and the other is an S polarized light component for which the plane of polarization is perpendicular to the Incident plane. The incident plane is defined as a plane which includes both an incident ray and a normal to the lens surface at the point where the incident ray strikes the lens surface.

It is known that the reflectivity of the optical element for the S polarized light component is higher than that for the P polarized light component, and therefore, the intensity of the S polarized light component in the exiting light becomes relatively lower. Thus, since the direction of the plane of polarization is based on the ratio of intensities of the two components, the plane of polarization rotates when the incident linearly polarized light includes both the P and S polarized light components.

On the other hand, when the plane of the polarization is parallel or perpendicular to the incident plane, since the P polarized light component or the S polarized light component is only included in the incident light, the plane of polarization would not rotate.

Referring to FIG. 2, the bright portions exclude zones along the horizontal and vertical diameters of the test lens. Since the transmission axis of the first polarizer 3 extends along the horizontal direction in FIG. 2, the incident planes in the zones along the horizontal and vertical diameters are almost parallel and perpendicular, respectively, to the plane of polarization, and therefore the light cannot transmit through the second polarizer 4, because the plane of polarization does not rotate in the aforementioned zones. Conversely since the incident planes have various directions depending on the points on the convex lens surface in those portions excepting the zones along the horizontal and vertical diameters, part of the incident light transmits through the second polarizer 4 because of the rotation of the plane of polarization.

Thus, the bright portions due to the optical rotation make it more difficult to detect birefringence. However, if the polarizers 3 and 4 are rotated, the bright portions due to the optical rotation change position accordingly such that when a plurality of frames of image data (representing various rotational angles of the polarizers 3 and 4) are composed to form one composite frame of image data, the effect of the rotation of the plane of polarization can be averaged.

On the other hand, the effect of the birefringence changes the phase difference between the two components (the S polarized light component and the P polarized light component). Therefore, the extraordinary rays do not change position even when the polarizers rotate. Accordingly, by composing a plurality of frames of image data, the effects of the birefringence accumulate and are emphasized.

Figure 3:
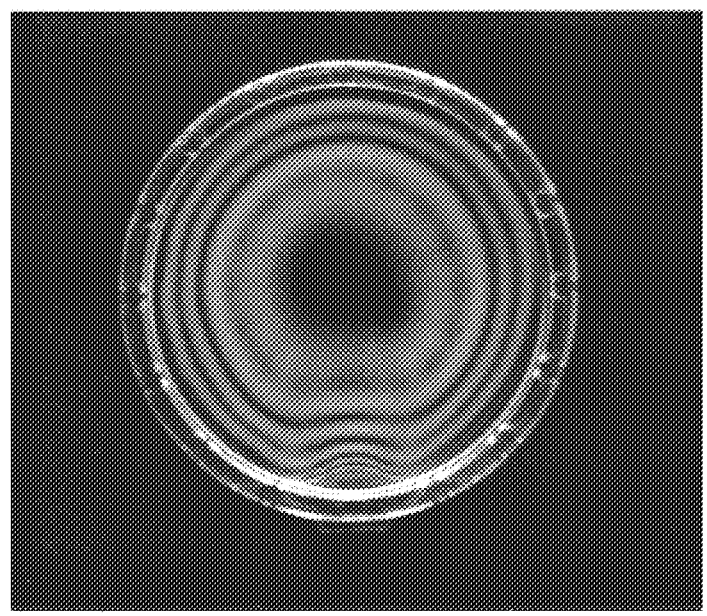
FIG. 3 is a photograph showing composite image data captured by the apparatus, in the case when the transmission axes of the polarizers are perpendicular.

FIG. 3 is a photograph showing a composite image data of eight (8) frames of the differentiated image data captured under the perpendicular condition. The concentric fringes represent the effect of the optical rotation, and the distortion of the fringes in the lower portion of the photograph represents birefringence due to strain In this way, it is easy to identify the birefringence using composite image data.

When the angle between the transmission axis of the polarizers 3 and 4 is set to 0 degrees (i.e., the parallel condition), light is normally transmitted through the second polarizer 4. In this case, the portions of the lens having birefringence and the portions at which dust or a flaw is present are dark in the captured image data of the test lens A. Thus, setting of 0 degrees for the angle between the transmission axes of the polarizers 3 and 4 is suitable to detect dust on the lens or flaws in the lens.

Figure 4:
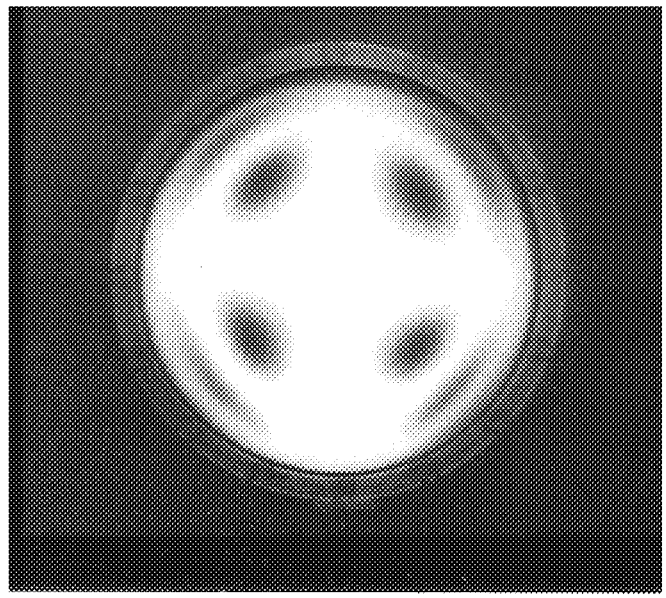
FIG. 4 is a photograph showing image data captured by the optical element inspecting apparatus before the composing process, in the case when the transmission axes of the polarizers are parallel.

FIG. 4 is a photograph showing the single-shot (frame) image data captured when the transmission axes of the polarizers 3 and 4 are parallel. The dark portions are caused mainly by the optical rotation as explained above. It is also difficult to find the effect of birefringence from FIG. 4.

Figure 5:
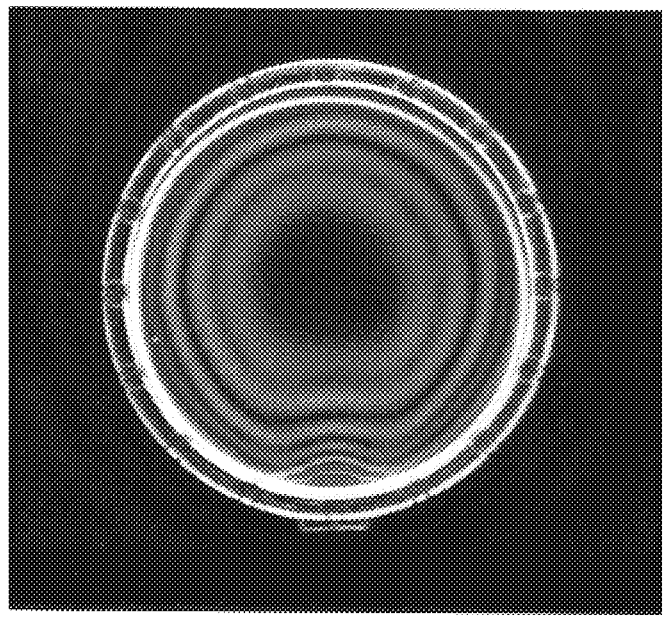
FIG. 5 is a photograph showing a composite image data captured by the optical element inspecting apparatus in the case where the transmission axes of the polarizers are parallel.

FIG. 5 is a photograph showing composite image data of eight frames of the differentiated image data captured as shown in FIG. 4. The concentric fringes represent the effect due to the optical rotation and the distortion of the fringes in the lower portion of the photograph represents birefringence due to strain. It is also easy to identify the birefringence using the composite image data.

Figure 6:
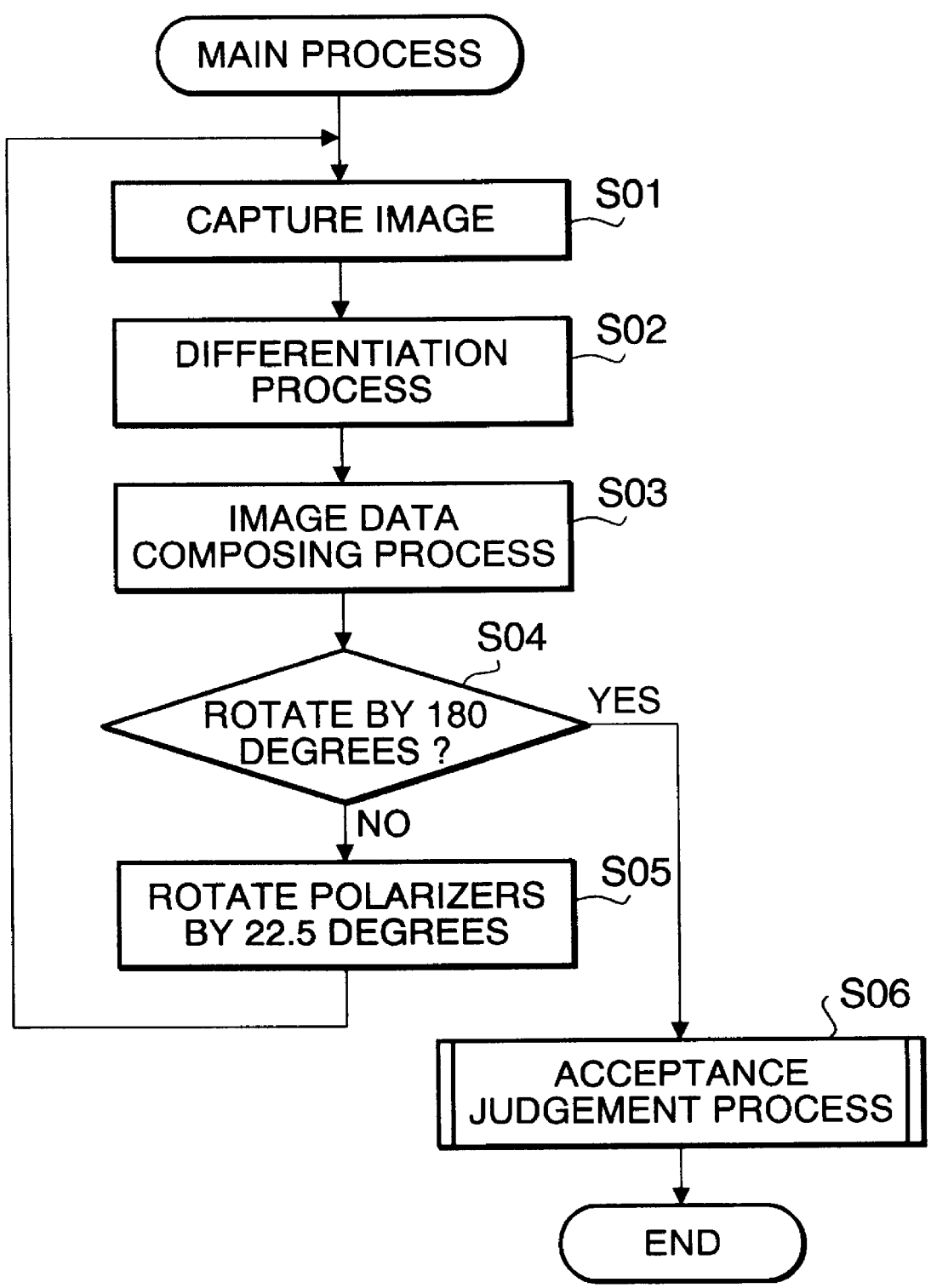
FIG. 6 is a flowchart showing a main process executed in the image processing unit of FIG. 1.
Figure 7:
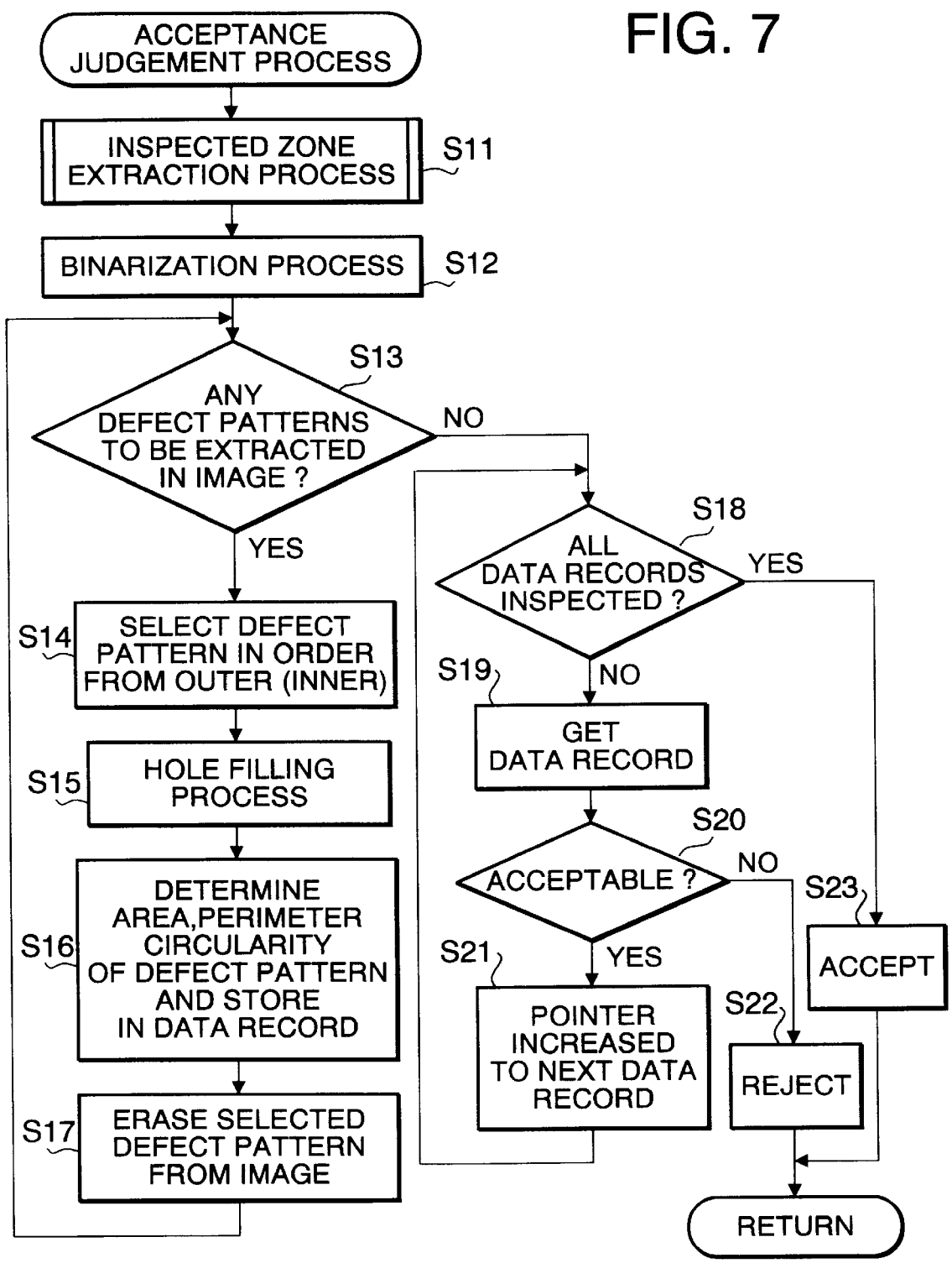
FIG. 7 is a flowchart showing the acceptance judgment process executed at step S06 of FIG. 6.
Figure 8:
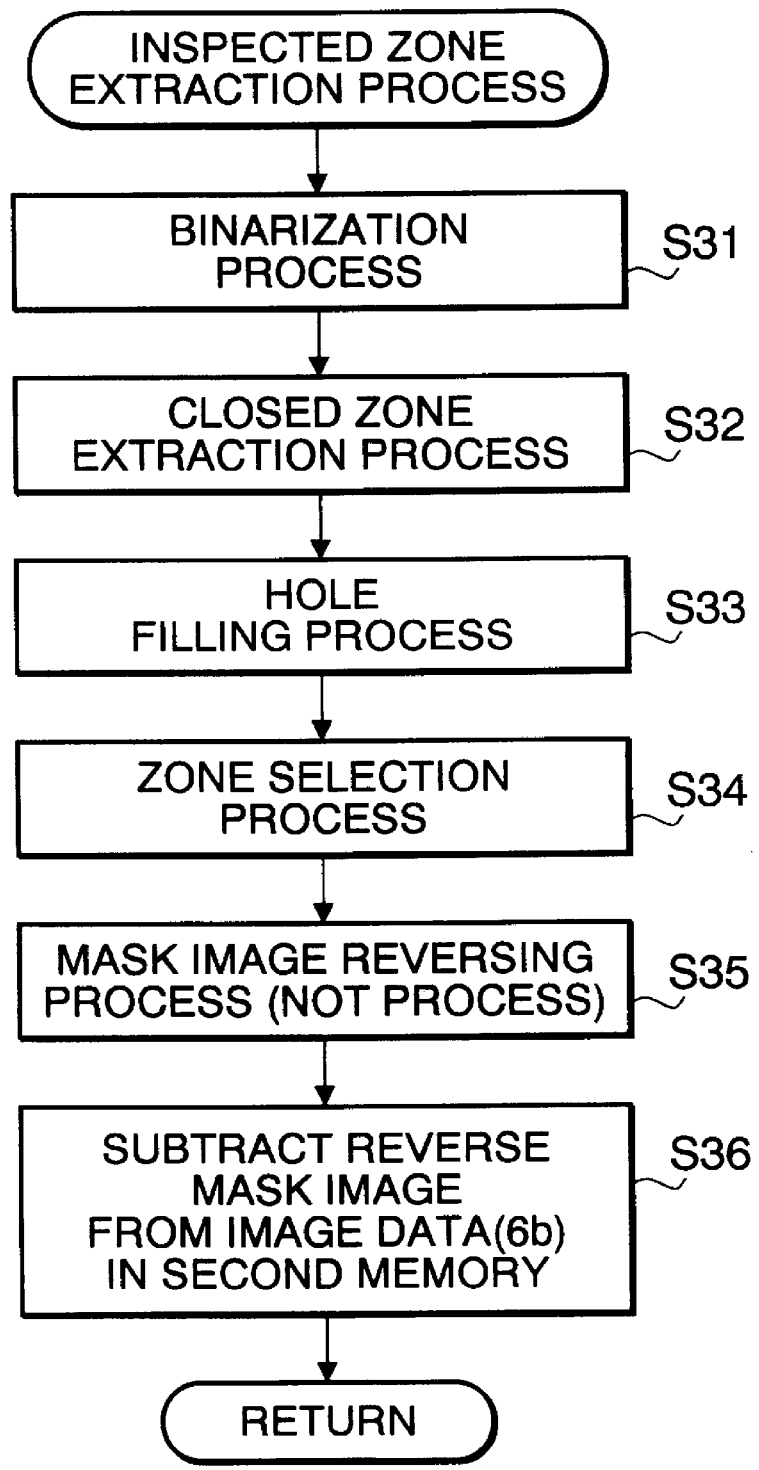
FIG. 8 is a flowchart showing the Inspected zone extraction process executed at step S11 of FIG. 7.

FIGS. 6 through 8 are flowcharts describing the operation of the first embodiment. FIG. 6 describes a main process, FIG. 7 describes an acceptance judgment process executed in step S06 in the main process, and FIG. 8 describes an inspected zone extraction process executed in step S11 of the acceptance judgment process.

The main process of FIG. 6 starts when a start switch (not shown) is turned ON. At step S01, image data is captured by the image detecting unit 5 and the brightness data of the captured image data is converted into digital image data having 8-bit (256) gradations. At step S02, the converted image data is differentiated and, then, at step S03, the image data is composed with the previous image data into composite image data. Steps S01 though S03 are repeated until the polarizers 3 and 4 have been rotated through 180 degrees at intervals of 22.5 degrees (Steps S04 and S05).

At step S01, the analog output from each of the pixels or the captured image data is converted into digital image data having 8-bit gradations and is stored in a corresponding address of the first frame memory 6a.

At step S02, a differentiation process is performed on the digital image data stored in the first frame memory 6a. That is, the difference of the brightness value of one pixel from that of the adjacent pixels at the left and upper sides thereof is calculated and the absolute value of the difference is set in the corresponding address of the second memory 6b as a differential value having 8-bit gradations. The differentiation process functions as a high pass filter to stress the edge portions of the image data, i.e., to emphasis brightness differences.

In the image composing process in step S03, the image processing unit 6 sums the differential values of the image data using the first and second frame memories 6a and 6b. As the process cycles through the loop from step S01 to step S05, the first-captured differentiated image data is stored into the second frame memory 6b and the second-captured differentiated image data stored in the first frame memory 6a is added to the first image data stored in the second frame memory 6b to make a composite image data of two image data and the composite image data is then stored in the second frame memory 6b. In the same manner, when the third through eighth image data are captured, each image data stored in the first frame memory 6a is added to the composite image data stored in the second frame memory 6b.

As a result of repeating the loop including steps S01 through S03 eight times, birefringence portions of the test lens in all areas are composed into the composite image data.

After the process of the loop of steps S01 through S05 is completed (YES at step S04), the acceptance judgment process is executed at step S06. The main process finishes when this acceptance judgment process is completed.

FIG. 7 shows the acceptance judgment process. At step S11, an inspected zone is extracted from the entire image data. In this process, as described below, the effective zone of the test lens is extracted (selected) from the overall image data captured by the image detecting element 5.

At step S12, the composed differential image data is converted into 1 bit digital data, i.e. is binarized, using an appropriate threshold level. The data for each pixel is classified into a white portion with a value of 255 or a black portion with a value of 0. In this step S12, graphic patterns within the image data are also identified.

In steps S13 through S17, characteristic graphic quantities are determined for each of the graphic patterns in the binarized image data.

First, if it is determined that there are graphic patterns to be extracted included in the binarized image data (Yes at step S13), the farthest pattern from the center of the image data is selected at step S14.

In the hole filling process at step S15, the black level pixels remaining within the closed area surrounded by the white level pixels which form the selected pattern are changed. This process is executed in the temporary memory (not shown) from the second frame memory 6b so that the original binarized image data is not changed.

At step S16, the selected graphic pattern is analyzed to produce numerical values such as area, perimeter and circularity. The area and the perimeter of the selected pattern are determined by counting the numbers of pixels and the circularity is calculated based on the area and the perimeter values.

In particular, the area of the pattern is calculated as the number of white level pixels. The perimeter is calculated as the total amount of the distances between pairs of adjacent white pixels on the perimeter of the selected pattern. The distance between adjacent pixels is "1" when adjacent pixels are collinear, i.e., the pixels are arranged along a row or column of the matrix of pixels. When adjacent white pixels form a corner, i.e., the pixels are arranged diagonally, the distance between the pixels is "√2". The circularity C is then calculated from the area A and the perimeter P according to the following equation:

$$C=4\pi *A /p^2.$$

At step S16, the values for the area, the perimeter and the circularity are stored into the character data memory 6c as characteristic graphic quantities for the selected graphic pattern. These numerical values for each graphic pattern are stored in fields of a data record. The character data memory 6c then contains a data record for each graphic pattern.

At step S17, the selected pattern is eliminated from the original binarized image data. Namely, the white level pixels corresponding to the selected pattern are converted to black level pixels.

After all of the graphic patterns in the image data have been selected and analyzed, the process enters the next loop of steps S18 through S23 in which the test lens is judged. In this example, the judgment is based on the circularity values. In particular, the circularity of a perfect circle is equal to 1 and the circularity becomes smaller as a pattern differs from a perfect circle. Since the image data obtained after the composition process includes concentric (circular) patterns as shown in FIG. 3 or 5 and these circular patterns are deformed when the test lens has birefringence, the amount of birefringence can be determined by checking the circularity of the circular patterns.

At step S18, it is determined whether all the data records In the character data memory 6c have been inspected, if not (No at step S18), the current data record for analysis (pointed at by a pointer) is read from the character data memory 6c at step S19 and the circularity is examined at step S20. The examination involves comparing the circularity value with a predetermined threshold value, for example, a threshold level of 0.9 can be used. If the circularity is higher than the threshold level, the pointer is moved to the next data record at step S21 and the process returns to step S18 and repeats until all data records have been examined.

Within the loop formed by step S18 to step S23, it the circularity of any one of the extracted patterns is lower than the threshold level, it is determined that the test lens under the current inspection should be rejected at step S22. On the other hand, when the circularities of all of the patterns are above the threshold level (No at step S18), it is determined that the test lens is acceptable at step S23. For example, at steps S22 and S23, the result is displayed on a display.

FIG. 8 shows a flowchart of the inspected zone extraction process executed at step S11 of FIG. 7. In steps S31 through S34 a mask pattern that corresponds to the image area of the test lens A is formed and in steps S35 and S36 the image data to be inspected is prepared.

In this process, the composed differential image data obtained by steps S01 through S05 of FIG. 6 is binarized in step S31 and closed zones are extracted in step S32. For the image data in the extracted zone, a hole filling process, a zone selection process and a mask image reversing process (NOT operation) are executed in steps S33, S34 and S35.

The binarization process is identical to step S12 of FIG. 7. In this case, the threshold level is determined so that the outline of the lens image appears as a closed white line.

In the closed zone extraction process at step S32, closed zones, i.e. zones that are surrounded by closed lines formed of white level pixels, are extracted. The numerical values of the pixels outside of the closed zones are set to 0 (black).

In the hole filling process of step 533, the numerical values of all pixels deemed to be inside the closed zone are set to 255 (white), i.e., any black level pixels which are surrounded by white level pixels are converted to white level pixels.

In the zone selection process at step S34, only the zones which are deemed to be essential are selected, and any other closed zones are deleted by converting them to black level pixels In this embodiment, the zone having the largest area is selected, since the largest area zone of white level pixels corresponds to the zone of the image of the test lens. The zone having the largest area shall be referred to hereinafter as the "mask pattern".

The NOT operation at step S35 inverts the mask pattern. That is, the current white level pixels are converted to black level pixels and the current black level pixels are converted to white level pixels.

At step S36, the reversed mask pattern is subtracted from the original 8-bit image data for each pixel. As a result of this process, the values of any pixels for which the reversed mask pattern is black level (0) remain equal to the values of the pixels in the original image data and the values of any pixels for which the reversed mask pattern is white level (255) are set to black level (0).

Thus, the process of FIG. 8 produces image data that has pixels with 8-bit gradations within the lens area and only black level pixels outside of the lens area.

A second embodiment of the optical element inspecting apparatus is now described.

Figure 9:
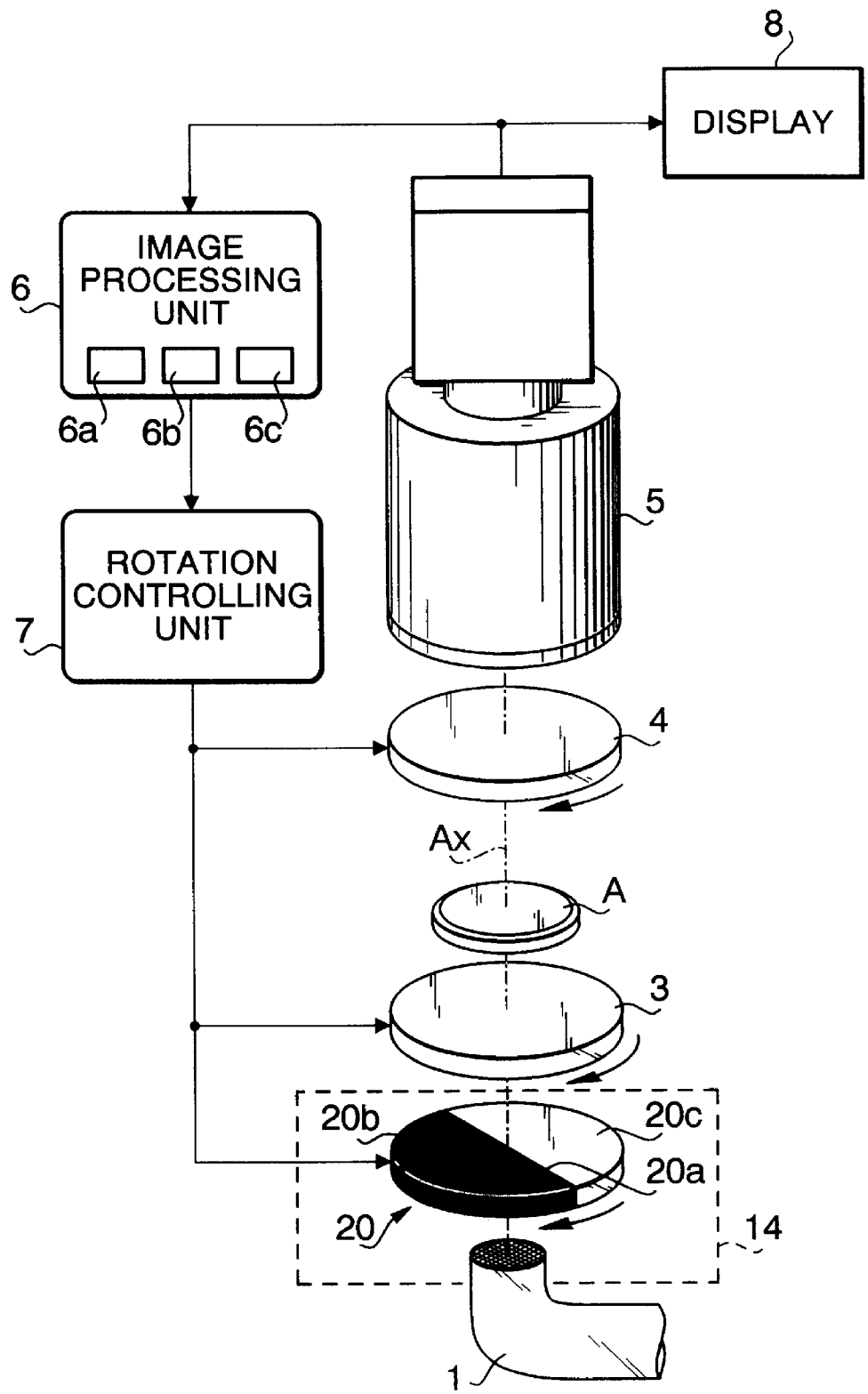
FIG. 9 is a perspective view and block diagram of a second embodiment of the optical element inspecting apparatus.
Figure 10:
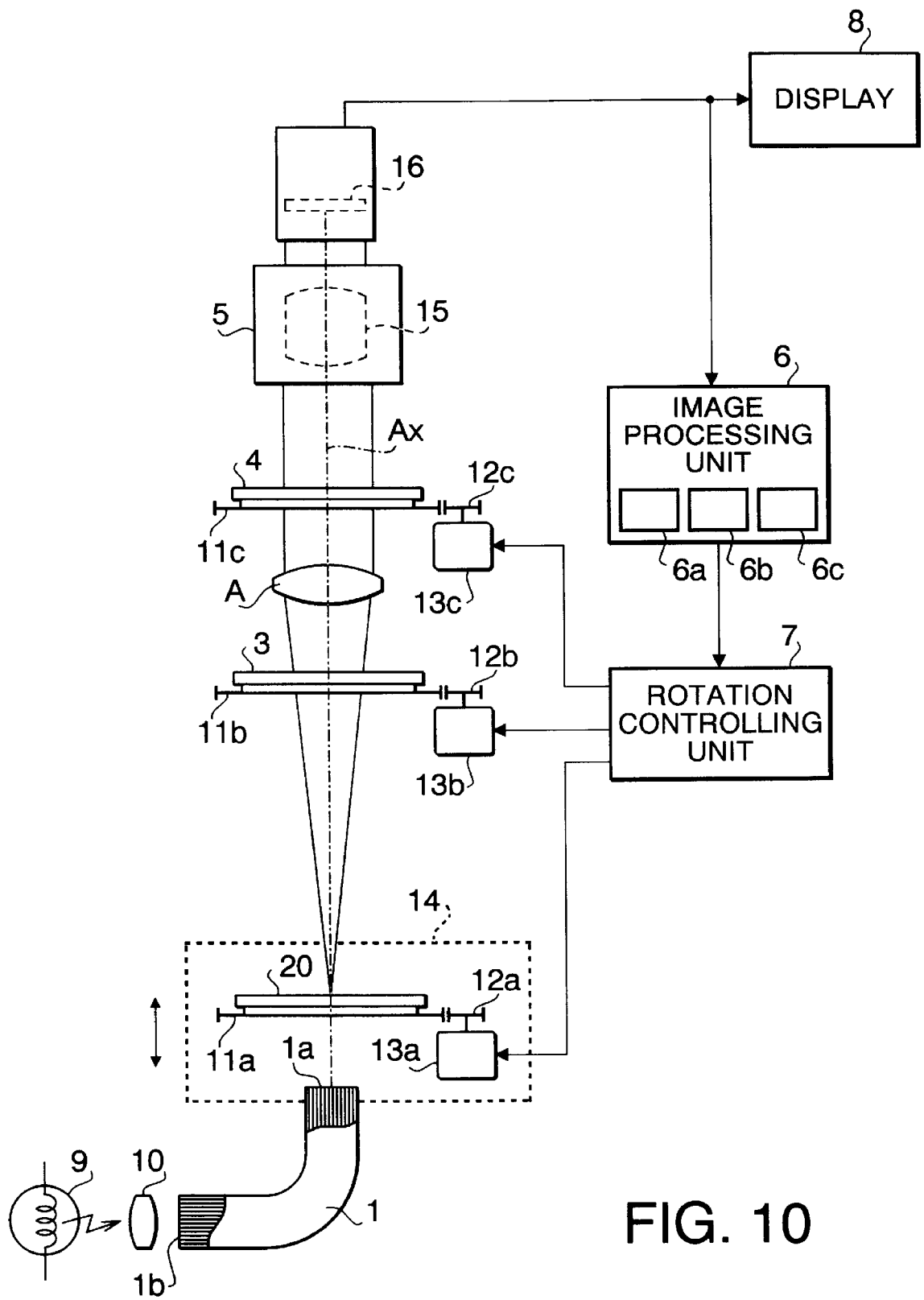
FIG. 10 is a detailed block diagram of the second embodiment of the optical element inspecting apparatus.

The second embodiment of the optical element inspecting apparatus is similar to the first embodiment except that a diffuser unit 14 and a display 8 are included as shown in FIG. 9. The arrangement of the polarizers 3 and 4, the photographing unit 5, the image processing unit 6 and the rotation controlling unit 7, are identical to the first embodiment. FIG. 10 shows the arrangement of FIG. 9 in more detail.

As shown in FIG. 9, the diffuser unit 14 includes a circular diffuser plate 20. The diffuser plate 20 is provided with a light intercepting portion 20b that covers half of the diffuser plate 20 and a light transmitting portion 20c. A straight edge (chord) of the light intercepting portion 20b defines a knife edge 20a that is a boundary line between the light intercepting portion 20b and the light transmitting portion 20c.

The diffuser plate 20 is rotatable about the rotation axis $A\chi$ that is the rotation axis for the polarizers 3 and 4. The rotation axis $A\chi$ is normal co the surface of the diffuser plate 20 and at the center thereof. Since the knife edge 20a is a diameter of the circular diffuser plate 20, the knife edge 20a intersects with the rotation axis $A\chi$.

Figure 11:
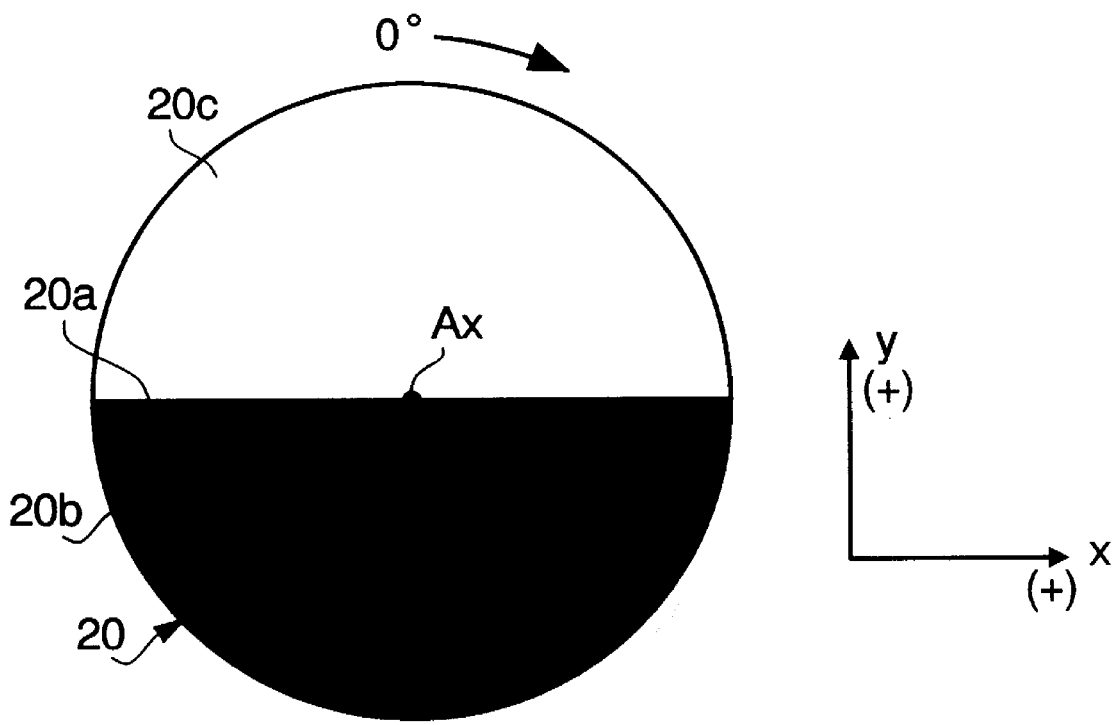
FIG. 11 is a plane view of the diffuser plate.

In a standard position, the light intercepting portion 20b covers the lower half of the diffuser plate 20 in FIG. 11 and the rotation angle of the diffuser plate 20 is defined as being 0 degrees. The rotation angles of 90, 180, and 270 degrees are determined from the standard position in a clockwise direction as shown by an arrow. In FIG. 11, an x axis is defined by the knife edge 20a when the rotation angle equals 0 degrees or 180 degrees, and a y axis is defined by the knife edge 20a when the rotation angle is equal to 90 degrees or 270 degrees. For each axis, the positive axis is indicated by a plus sign in FIG. 11.

In this embodiment, the direction of the knife edge 20a in a plane perpendicular to the rotation axis $A\chi$ is aligned with the direction of the transmission axis of the first polarizer 3. However, alternatively, these directions can be set at a predetermined angle in relation to each other about the rotation axis $A\chi$.

Returning to FIG. 10, the light emitted from a light source 9 is condensed by a condenser lens 10 to be incident on the light guide fiber bundle 1 at an incident end 1b. The light is transmitted by the fiber bundle 1 and exits from an exit end 1a of the fiber bundle 1. The exit light is then diffused by the diffuser plate 20 and half of the light is blocked by the light intercepting portion 20b The remaining half of the light is incident on the first polarizer 3 and is converted into linearly polarized light. The light transmits through a test lens A and the second polarizer 4 and is then detected by the photographing unit 5.

As above, the test lens system must have positive power so that the front focal point of the test lens can be located on the diffuser plate 20 As such, when a positive test lens A (as shown in FIG. 10) is inspected, only the zest lens A is located between the polarizers 3 and 4. On the other hand, if the test lens has negative power, a supplementary lens is required to ensure that the total optical system has positive power. In this case, both the negative test lens and the supplementary lens, which compose the test lens system, are located between the polarizers 3 and 4.

The photographing unit 7 is provided with a photographing lens 15 and an image detecting element 16. It is preferable that the rotation axis $A\chi$ of the diffuser plate 20 is coaxial with the optical axis of the photographing lens 15.

The image detecting element 16 captures data of an image formed by the photographing lens 15. The image detecting element 16 and the test lens A are optically conjugate with respect to the photographing lens 15. That is, the image of the test lens A is formed on the image detecting element 16. The image detecting element 16 is formed as a two-dimensional array of pixels. After an image data is captured, the image data is output from the image detecting element 16 as analog brightness data, i.e. gray-scale data, for each pixel.

The image data output from the image detecting element 16 is sent to both a display 8, such as a CRY, and the image processing unit 6. The image data is displayed on the display 8 as a monochrome picture pattern in which the tone at each point represents the brightness data of a corresponding pixel.

The diffuser plate 20 is mounted on a first annular turn table 11a that has a gear around its circumference. The gear engages a pinion 12a of a first motor 13. In a similar way, the first and second polarizers 3 and 4 are mounted on second and third annular turn tables 11b and 11c that have gears around their circumferences. The gears of the second and third turn tables engage pinions 12b and 12c of the motors 13b and 13c respectively. The rotation controlling unit 7 drives the motors 13a, 13b and 13c so that the polarizers 3 and 4 and the diffuser plate 20 rotate in synchronism with one another.

The diffuser unit 14 that includes the diffuser plate 20 with the first turn table 11a and the first motor 13a is movable along the rotation axis $A\chi$ in order to adjust for the power of the test lens A such that the focal point of the test lens A coincides with the diffuser plate 20. The optical fiber bundle 1 is flexible and sufficiently long to allow such movement and the optical fiber bundle 1 follows the movement of the diffuser unit 14 so that appropriate illumination will always be provided.

The test lens A is set such that its optical axis coincides with the rotation axis $A\chi$, and defects in the test lens can be effectively detected by capturing a plurality of frames of image data (for different angles of the light intercepting portion 20b and the polarizers 3 and 4) with the image detecting element 16.

In the second embodiment, an inspector sets the test lens in the optical path of the apparatus, aligns the test lens such that the optical axis of the test lens is coaxial to the rotation axis $A\chi$, and adjusts the position of the diffuser unit 14 along the rotation axis $A\chi$. The alignment of the test lens and the adjustment of the diffuser unit 14 are, for example, performed manually with reference to the image data displayed on the display 8. Also, the first and second polarizers 3 and 4 are removed from the optical path during the alignment process.

During adjustment, the light source 1 is turned on to illuminate the diffuser plate 20. As a result, the image data captured by the image detecting element 16 is shown on the display 8. The inspector then adjusts the diffuser unit 14 along the rotation axis $A\chi$ while observing the displayed image data.

In particular, the inspector observes that the light intensity distribution of the displayed image data varies depending on the distance between the focal point of the optical element and the diffuser plate 20 along the rotation axis $A\chi$.

For example, FIGS. 12a through 12e are photographs which indicate actual captured image data as the diffuser unit 14 is moved along the rotation axis $A\chi$, i.e., as the distance between the focal point of the test lens A and the diffuser plate 20 varies. In this case, the test lens A is a rectangular shaped biconvex lens made of a synthetic resin of which front and rear surfaces are spherical. Black-white tones represent relative brightness. These image data show the condition when the light intercepting portion 20b is at the standard position (i.e. when the rotation angle equals 0 degrees as shown in FIG. 11). In the captured image data, the x-y axes are defined in the same manner as those for the diffuser plate 20. However, the positive x axis appears reversed when compared to that for the diffuser plate 20 (in FIG. 11) since the point of view is reversed (i.e. now viewed from the illumination unit 14 side).

In FIGS. 12a through 12e, an image pattern 100 of the test lens is formed as a real inverted image, as shown by a dotted line, and an image pattern 200 of the light intercepting portion 20b is formed as a real inverted image by the light that does not pass through the test lens. The image pattern 100 of the test lens is formed in an in focus condition and the image pattern 200 of the light intercepting portion 20b (outside of the lens) is formed in an out of focus condition in the background of the image pattern 100. Also, the image pattern 100 of the test lens may include a shading image pattern of the light intercepting portion 20b, as formed by the light transmitted through the test lens.

Figure 12A:
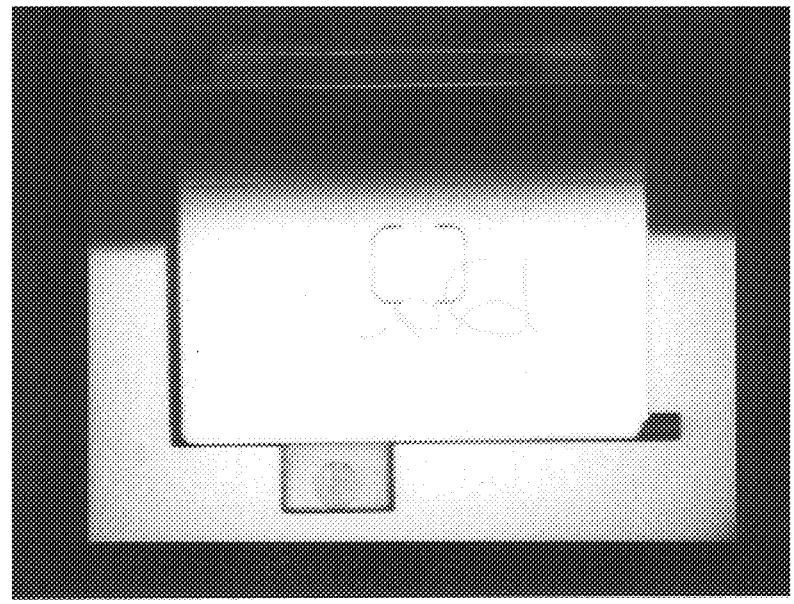
FIGS. 12a through 12e are photographs showing image data captured by the optical element inspecting apparatus of the second embodiment when a diffuser unit is being adjusted.
Figure 12B:
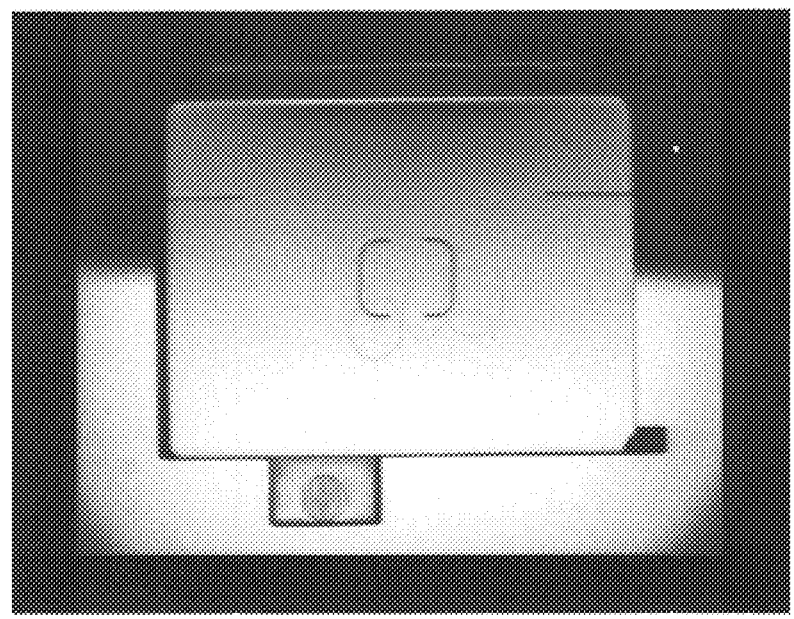

In the case when the focal point of the test lens is positioned behind the diffuser plate 20, at the light guide fiber bundle 1 side, i.e., the distance between the test lens and the diffuser plate 20 is smaller than the standard length, the shading image pattern is formed as a real inverted image inside the image pattern 100 as shown in FIGS. 12a and 12b. In this case, the smaller the distance (i.e. the larger the distance from the standard length), the more distinct the shading image pattern. The shading image pattern in FIG. 12a is more distinct than that in FIG. 12b because of the smaller distance.

Figure 12C:
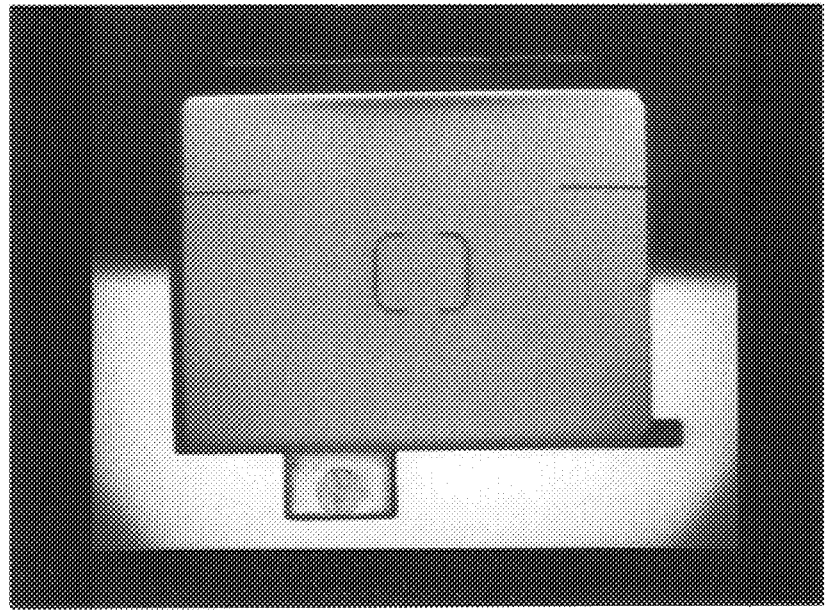

In the case when the focal point of the test lens coincides with the diffuser plate 20, that is, the standard length for inspection, the brightness distribution inside the image pattern 100 of the test lens is uniform as shown in FIG. 12c.

Figure 12D:
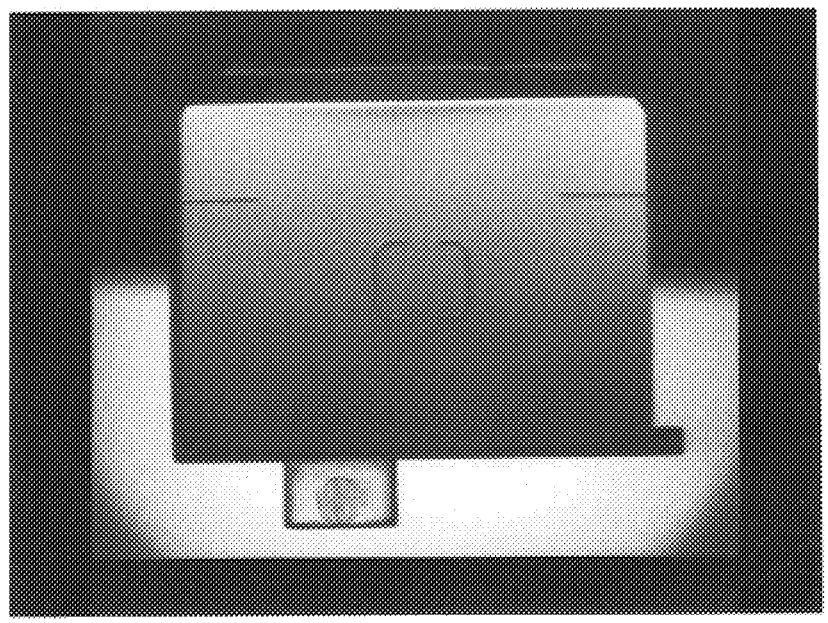
Figure 12E:
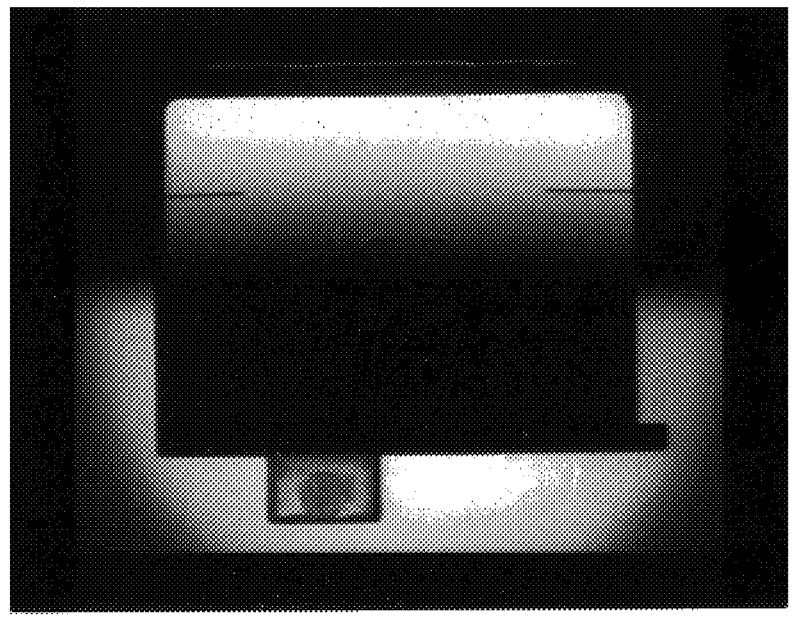

In the case when the focal point of the test lens is positioned in front of the diffuser plate 20 at the image photographing unit 5 side, i.e., when the distance between the test lens and the diffuser plate 20 is larger than the standard length, the shading image pattern of the light intercepting portion 20b is formed as a real correct image inside the image pattern 100, as shown in FIGS. 12d and 12e. In this case, the larger the distance is (i.e. the larger the distance from the standard length), the more distinct the shading image pattern is The shading image pattern in FIG. 12e is more distinct than that in FIG. 12d because of the larger distance.

Accordingly, the diffuser unit 14 can be manually adjusted to ensure that the focal point of the test lens coincides with the diffuser plate 20 based on the image data displayed on the display 8.

During the adjustment of the diffuser unit 14, if, as shown in FIG. 12a or 12b, the shading image pattern in the image pattern 100 appears in the same orientation as the image pattern 200 of the light intercepting portion 20b outside the lens image pattern 100, it means that the diffuser unit 14 is too close to the test lens A. The diffuser unit 14 is thus moved away from the test lens A. On the other hand, if, as shown In FIG. 12d or 12e, the shading image pattern in the image pattern 100 appears in an opposite orientation to the image pattern 200 of the light intercepting portion 20b outside the lens image pattern 100, it means the diffuser unit 14 is too far from the test lens A. The diffuser unit 14 is thus brought closer to the test lens A. When the shading image pattern essentially disappears from the area within the image pattern 100 as shown in FIG. 12c, the adjustment is stopped since the diffuser unit 14 will then be at the standard position.

Figure 13:
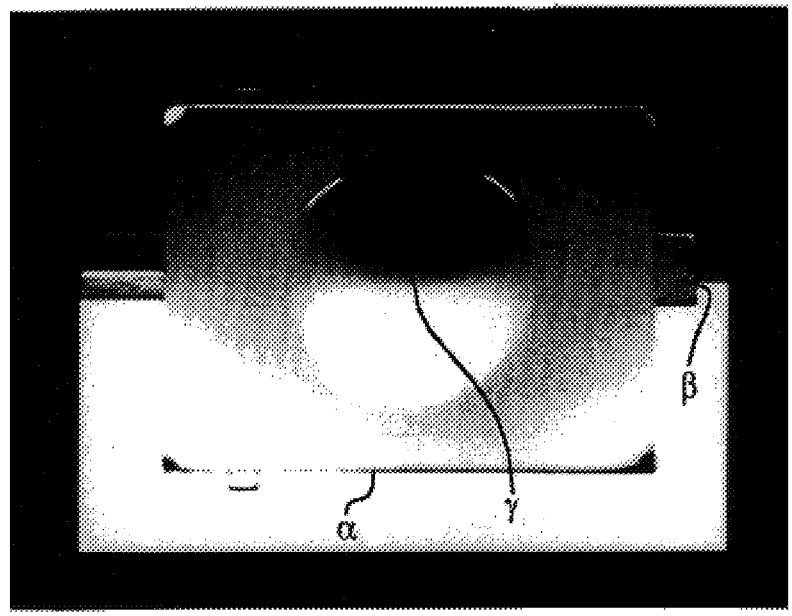
FIG. 13 is a photograph showing the image data captured by the optical element inspecting apparatus of the second embodiment when an optical element with a refractive index anomaly is inspected.

As a result of the adjustment, if the test lens is acceptable and has no defects, the brightness distribution inside the image pattern 100 is uniform. However, if the test lens has an inhomogeneous refractive power distribution due to a refractive index anomaly or a shape detect at the surface, the focal length at the anomalous part will differ from the focal length at the normal part. Thus, as shown in FIG. 13, an anomalous image pattern 101 of the light intercepting portion 20b will appear at the anomalous part.

After the adjustment of the diffuser unit 14 along the rotation axis $A\chi$, the centering process begins, in which the test lens A is aligned, so that the optical axis of the test lens A coincides with the rotation axis $A\chi$. The alignment is also manually executed with reference to the image pattern indicated on the display 8. If the optical axis of the test lens A is off-center from the rotation axis $A\chi$, the brightness distributions in the off-center direction will change according to the rotation of the diffuser plate 20. The alignment is completed when the brightness distributions along the x and y directions are constant regardless of the rotation angle of the diffuser plate 20.

Under the condition where the focal point of the test lens A meets the diffuser plate 20 and the optical axis of the test lens is coaxial to the rotation axis $A\chi$, the polarizers 3 and 4 are attached as shown in FIGS. 9 and 10 and the inspection process is executed. The transmission axes of these polarizers may be either perpendicular or parallel to each other, as described previously.

In the second embodiment the test lens A is also inspected based on the composite differentiated image data as in the first embodiment.

Figure 14:
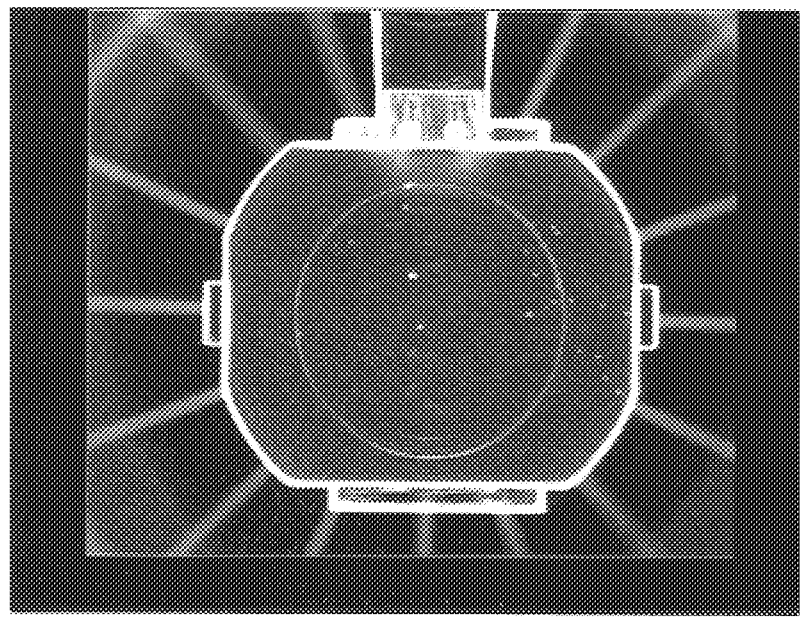
FIG. 14 is a photograph showing composite image data captured by the optical element inspecting apparatus of the second embodiment, in the case when the transmission axes of the polarizers are parallel.

FIG. 14 shows composite image pattern in a case where the transmission axes of the polarizers are parallel. And FIG. 15 shows the graphic patterns extracted from the pattern of FIG. 14.

Figure 15:
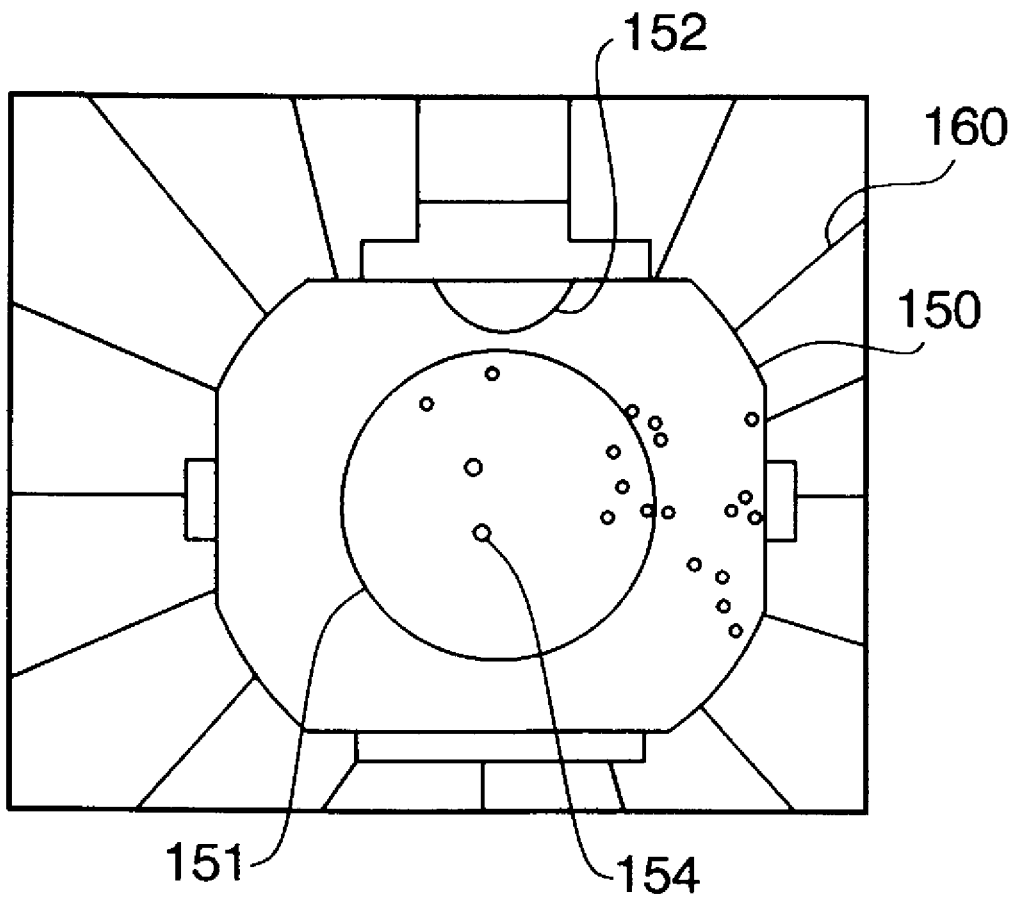
FIG. 15 is a drawing showing the extracted graphic patterns of FIG. 14.

In FIG. 15, the reference number 150 indicates an outline of the test lens A, the reference number 151 indicates the edge line of an inhomogeneous refractive power distribution such as that shown in FIG. 13, the reference number 152 indicates birefringence due to strain of the material, and the reference number 154 shows dust on the lens surface. The radiating straight lines 160 are image patterns of the knife edge 20a. In this parallel condition, three kinds of defects, which are the inhomogeneous refractive power distribution, the birefringence and the surface defect, can be detected. In particular, this parallel condition can also be used to detect surface detects such as dust or flaws.

Figure 16:
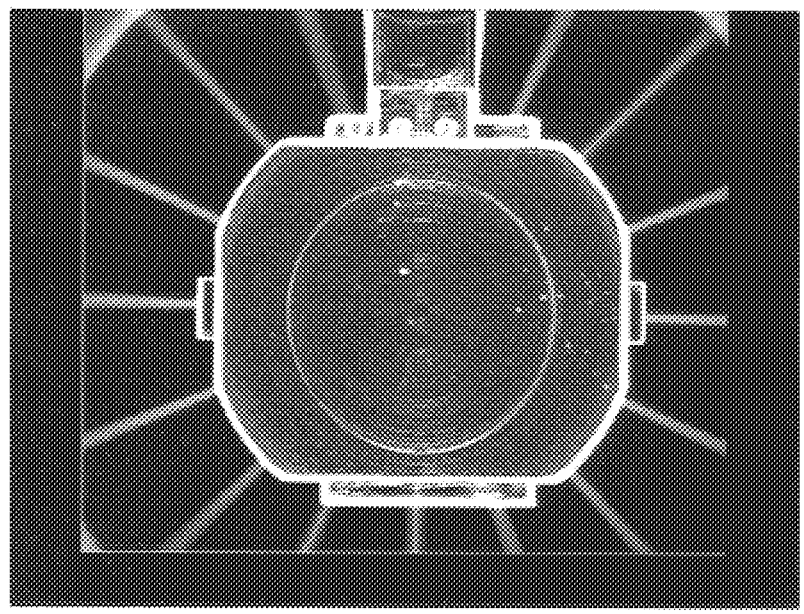
FIG. 16 is a photograph showing composite image data captured by an apparatus similar to the second embodiment, but without polarizers.
Figure 17:
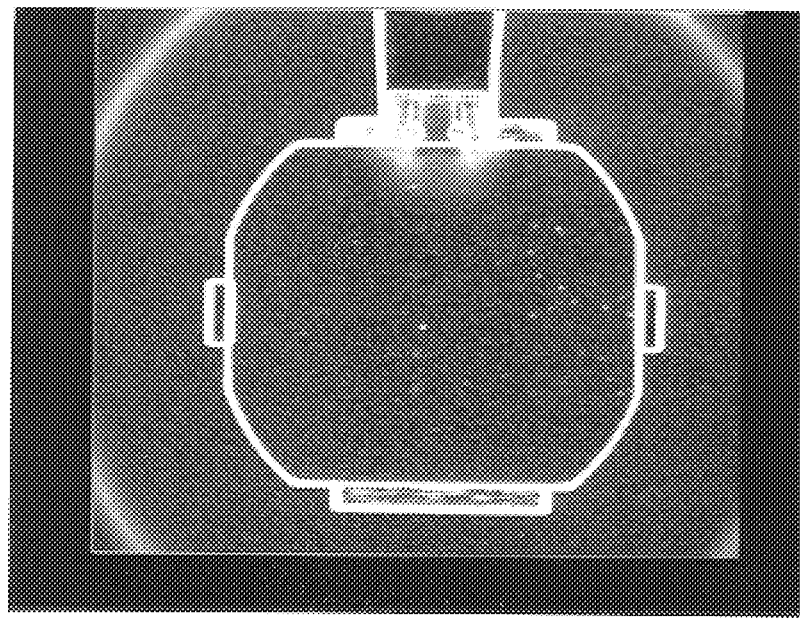
FIG. 17 is a photograph showing composite image data captured by the apparatus of the first embodiment, in the case when the transmission axes of the polarizers are parallel.
Figure 18:
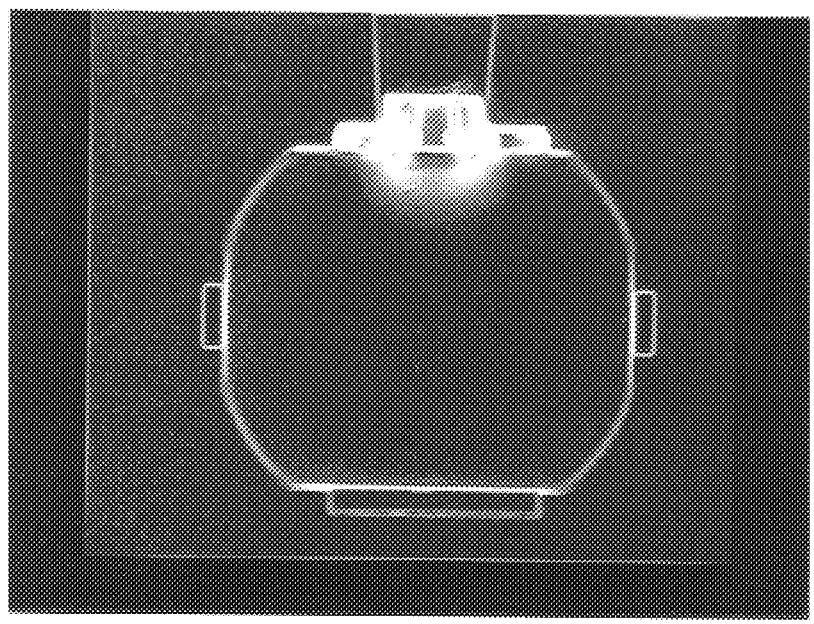
FIG. 18 is a photograph showing a composite image data captured by an optical element inspecting apparatus of the first embodiment, in the case when the transmission axes of the polarizers are perpendicular.

The second embodiment (using the parallel condition) has advantages over the first embodiment and other methods in that a variety of defects can be detected simultaneously. For example, FIG. 16 is a photograph showing a composite image captured by an apparatus similar to the second embodiment but that does not include the polarizers 3 and 4. In this case, although some defects, such as surface defects and the inhomogeneous refractive power distribution, can be seen, birefringence cannot be detected. Further, in the case of the first embodiment using a parallel condition, as shown in FIG. 17, birefringence and surface defects can be detected, however, inhomogeneous refractive power distribution cannot be detected. Still further, FIG. 18 shows the composite image data for a case where the first embodiment is used with a perpendicular condition. In this case, the portion having birefringence is emphasized more so than in FIG. 17, however, other defects such as the surface defects and the inhomogeneous refractive power distribution are not detected. Thus, the first embodiment using a perpendicular condition is preferable for inspecting birefringence, however, the second embodiment using a parallel condition is preferable for a general inspection of a variety of defects.

Figure 19:
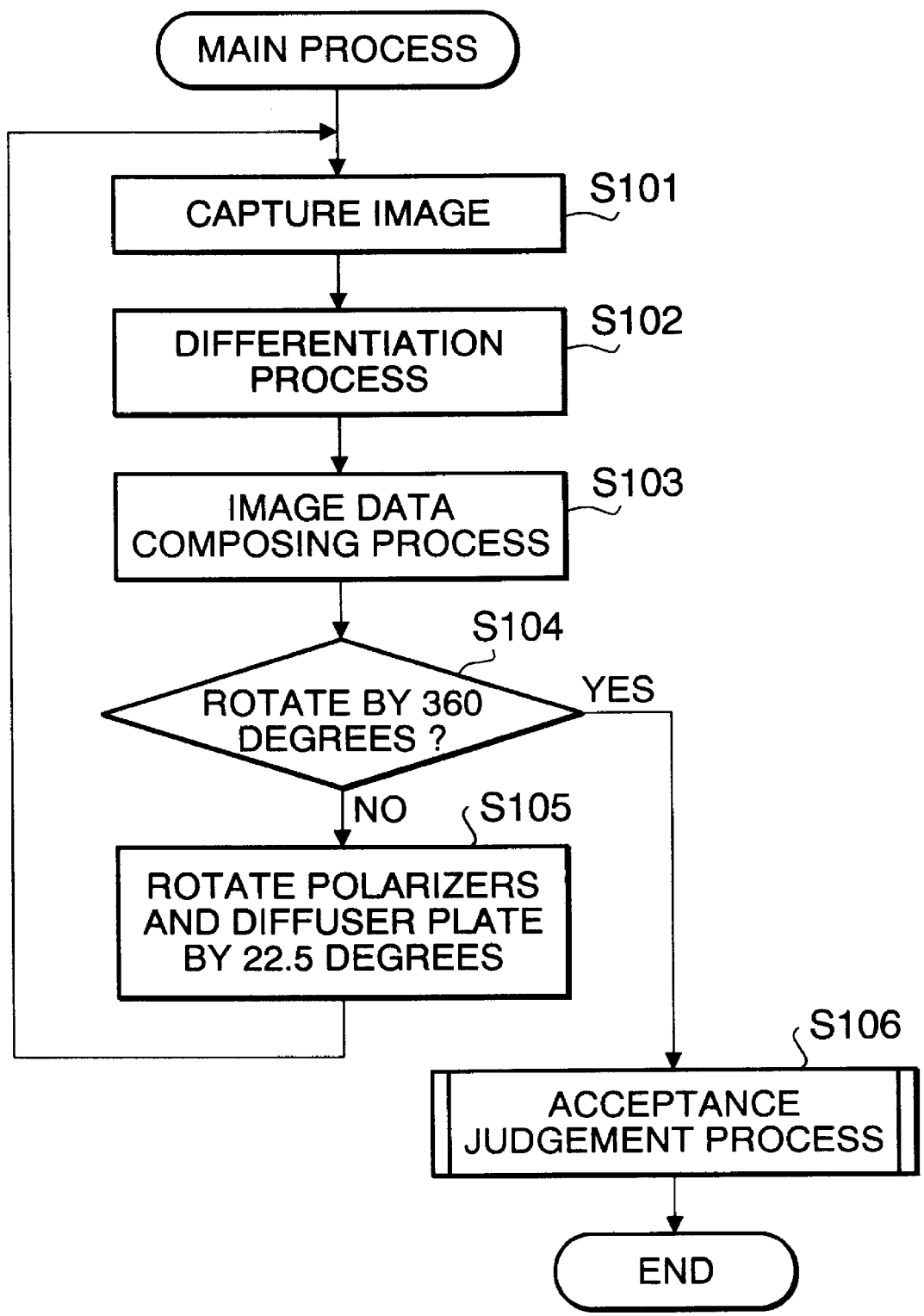
FIG. 19 is a flowchart showing the main process executed in the image processing unit of FIG. 9.
Figure 20:
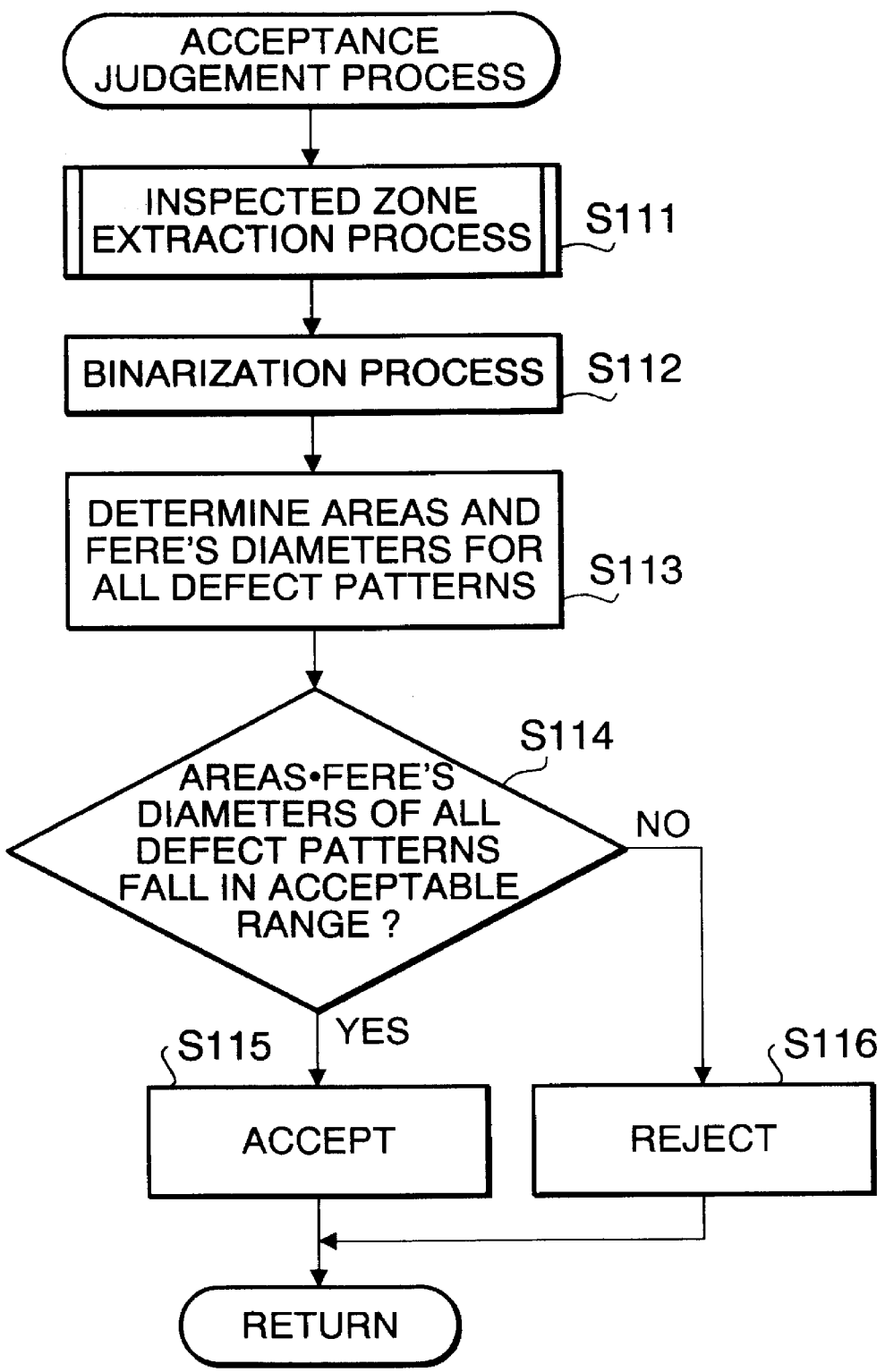
FIG. 20 is a flowchart showing the acceptance judgment process executed at step S106 of FIG. 19.

The inspection process of the second embodiment is described with reverence to the flowcharts shown in FIGS. 19 and 20. The inspection process is executed using the parallel condition of the polarizers. The process is almost identical to the first embodiment.

In the main process shown in FIG. 19, the image data is captured and converted to 8-bit digital data at step S101, the differentiation process and the image data composing process are executed at steps S102 and S103 These steps S101 through S103 are repeated at 22.5 degrees intervals of rotation of the diffuser plate 20 and the polarizers 3 and 4 until a 360 degree rotation is completed (steps S104 and S105).

After the 360 degree rotation is completed, i.e., sixteen (16) image data are composed, it is determined whether the test lens is acceptable or not in the acceptance judgement process at step S106.

FIG. 20 shows the acceptance judgment process of step 106 in FIG. 19. At step S111, the inspected zone is extracted from the overall image data. This process is identical to that of the first embodiment shown in FIG. 8.

At step S112, the composed differential data is converted into 1-bit digital data, i.e. is binarized, using an appropriate threshold level. The value for each pixel is set as a white level with a value of 255 or a black level with a value of 0. Also in step S112, graphic patterns in the image data are extracted.

At step S113, the area and Fere's diameter are determined for each of the graphic patterns extracted from the binarized image data. Fere's diameter is one of the numerical values indicating the character of each of the graphic patterns. It means a diameter of the pattern along the vertical or perpendicular direction corresponding to the matrix of pixels.

At the step S114, it is determined whether the detected areas and Fere's diameters of the extracted graphic patterns fall in the acceptable range.

If the area and Fere's diameter of all of the extracted pattern is lower than a predetermined threshold level in step S114, it is determined the test lens under the current inspection is acceptable in step 115. On the other hand, if the area and Fere's diameter of at least one of the patterns are above the threshold level, it is determined that the test lens should be rejected at step S116. For example, at steps S115 and S116, the examined result is displayed on the display 8.

Although the structure and operation of an optical element inspecting apparatus is described herein with respect to the preferred embodiments, many modifications and changes can be made without departing from the spirit and scope of the invention.

The present disclosure relates to subject matters contained in Japanese Patent Application on Nos. HEI 7-263327 filed on Oct. 11, 1995, HEI 7-326121 filed on Dec. 14, 1995, HEI 8-182557 filed on Jul. 11, 1996, and HEI 8-182558 filed on Jul. 11, 1996, which are expressly incorporated herein by reference in their entirety.

What is claimed is:

1. An optical element inspecting apparatus for detecting a defect of an optical element, said apparatus comprising:

an illuminating unit for illuminating said optical element;

an image capturing unit which receives light output by said illuminating unit via said optical element;

two polarizers located in an optical path between said illuminating unit and said image capturing unit, positioned such that said optical element is located between said polarizers;

a rotation device for rotating said polarizers such that respective transmission axes of said two polarizers rotate in planes which cross said optical path while keeping a constant angle between said respective transmission axes;

a controller for controlling said image capturing unit and said rotation device to capture image data representative of images formed by the light transmitted through said polarizers, said controller controlling said image capturing unit to capture image data at a plurality of angular positions within a 180° rotation of said polarizers;

means for composing the image data captured by said image capturing unit; and means for representing at least one characteristic of patterns included in said image data as a numerical value, and for comparing said numerical value with a predetermined reference value in order to judge whether said optical element is acceptable or not.

2. The optical element inspecting apparatus according to claim 1, further comprising a diffuser plate located between said illuminating unit and said optical element.

3. The optical element inspecting apparatus according to claim 1, wherein said polarizers are arranged so that the respective transmission axes are perpendicular to each other.

4. The optical element inspecting apparatus according to claim 1, wherein said polarizers are arranged so that the respective transmission axes are parallel to each other.

5. The optical element inspecting apparatus according to claim 1, further comprising means for emphasizing brightness differences within the image data composed by said composing means.

6. The optical element inspecting apparatus according to claim 5, wherein said emphasizing means performs a differentiation process on the brightness value of each pixel of said image data, wherein in said differentiation process the brightness value of each pixel of said image data is converted into a difference value determined by comparing the brightness value of one pixel with corresponding adjacent pixels.

7. The optical element inspecting apparatus according to claim 1, wherein said representing means represents a circularity of said patterns as a numerical value.

8. The optical element inspecting apparatus according to claim 1, further comprising:
   a photographing unit, said photographing unit including a photographing lens and said image capturing unit, said image capturing unit including an image detecting element.

9. The optical element inspecting apparatus according to claim 8, said image detecting element and said optical element being located at positions optically conjugate with respect to said photographing lens.

10. The optical element inspecting apparatus according to claim 1, wherein an angle between a transmission axis of a first of said two polarizers and a transmission axis of a second of said two polarizers is one of either 90° or 0°.

11. An optical element inspecting apparatus for detecting a defect of an inspected element, said apparatus comprising:
   an illuminating unit for illuminating an optical system including at least said optical element, said optical system havingpositive power;
   an image capturing unit located opposite to said illuminating unit with said optical system therebetween;
   a light intercepting member located between said illuminating means and said optical system to intercept a part of the light emitted from said illuminating unit, said light intercepting member being located at the focal point of said optical system;
   a pair of polarizers located in an optical path between said illuminating unit and said image capturing unit, positioned such that said optical system is located between said pair of polarizers;
   a rotation device for rotating said pair of polarizers so that respective transmission axes of said pair of polarizers rotate in planes perpendicular to said optical path while keeping a constant angle between said respective transmission axes;
   a controller for controlling said image capturing unit and said rotation device to capture data of images formed by the light transmitted through said pair of polarizers and said optical system for a plurality of different rotational positions of said pair of polarizers; and
   means for composing the image data captured by said image capturing unit.

12. The optical element inspecting apparatus according to claim 11, further comprising a diffuser plate located between said illuminating unit and said optical system.

13. The optical element inspecting apparatus according to claim 11, wherein said controller controls said image capturing unit to capture image data at a plurality of annular positions within a 360 degree rotation of said pair of polarizers.

14. The optical element inspecting apparatus according to claim 11, wherein said pair of polarizers are arranged so that said respective transmission axes are perpendicular to each other.

15. The optical element inspecting apparatus according to claim 11, wherein said polarizers are arranged so that said respective transmission axes are parallel to each other.

16. The optical element inspecting apparatus according to claim 11, wherein a light transmitting portion and a light intercepting portion of said light intercepting member are separated by a straight line, and wherein said rotation device rotates said intercepting member about a rotation axis that intersects with said straight line.

17. The optical element inspecting apparatus according to claim 15, wherein the optical axis of said optical system coincides with said rotation axis of said intercepting member.

18. The optical element inspecting apparatus according to claim 17, wherein said rotation device rotates said intercepting member in synchronism with the rotation of said pair of polarizers.

19. The optical element inspecting apparatus according to claim 11, further comprising means for emphasizing brightness differences of the image data composed by said composing means.

20. The optical element inspecting apparatus according to claim 19, wherein said emphasizing means performs a differentiation process on the brightness value of each pixel of said image data, wherein in said differentiation process the brightness value of each pixel of said image data is converted into a difference vale determined by comparing the brightness value of one pixel with corresponding adjacent pixels.

21. The optical element inspecting apparatus according to claim 20, further comprising means for representing at least one characteristic of patterns included in said image data as a numerical value, and means for comparing said numerical value with a predetermined reference value in order to judge whether said optical element is acceptable or not.

22. The optical element inspecting apparatus according to claim 19, further comprising means for representing at least one characteristic of patterns included in said image data as a numerical value, and means for comparing said numerical value with a predetermined reference value in order to judge whether said optical element is acceptable or not.

23. The optical element inspecting apparatus according to claim 11, further comprising means for representing at least one characteristic of patterns included in said image data as a numerical value, and means for comparing said numerical value with a predetermined reference value in order to judge whether said optical element is acceptable or not.

* * * * *

UNITED STATES PATENT AND TRADEMARK OFFICE
CERTIFICATE OF CORRECTION

PATENT NO. : 5,828,500
DATED : October 27, 1998
INVENTOR(S) : Atsushi KIDA et al.

It is certified that error appears in the above-identified patent and that said Letters Patent is hereby corrected as shown below:

At column 15, line 32 (claim 11, line 5)
"havingpositive" should be ---having positive---.

At column 16, line 3 (claim 13, line 3)
change "annular" to ---angular---.

At column 16, line 36 (claim 20, line 6)
change "vale" to ---value---.

Signed and Sealed this

Twenty-fifth Day of May, 1999

Attest:

Q. TODD DICKINSON

*Attesting Officer*   *Acting Commissioner of Patents and Trademarks*